United States Patent [19]

Kennedy

[11] Patent Number: 4,973,162
[45] Date of Patent: Nov. 27, 1990

[54] RING LASER GYROSCOPE READOUT

[76] Inventor: Thomas W. Kennedy, 134 Wildwood Ave., Montclair, N.J. 07043

[21] Appl. No.: 497,349

[22] Filed: Mar. 22, 1990

[51] Int. Cl.$^5$ ............................................... G01B 9/02
[52] U.S. Cl. .................................................. 356/350
[58] Field of Search ...................... 356/350; 372/94, 38

[56] References Cited

U.S. PATENT DOCUMENTS

| | | | |
|---|---|---|---|
| 4,257,015 | 3/1981 | Ljung | 356/350 |
| 4,422,762 | 12/1983 | Hutchings et al. | 356/350 |
| 4,473,297 | 9/1984 | Simpson et al. | 356/350 |

Primary Examiner—Frank Gonzalez
Assistant Examiner—Susan S. Morse

[57] ABSTRACT

A triangular ring laser gyroscope which has three readout subassemblies with a circuit for using the best two out of the three readings. The gyroscope includes a block having corners with three mirrors, anode and cathode means, three readout subassemblies with a circuit having three adders and three subtractors and three switch units which provide the best two out of the three readings for an average output reading.

12 Claims, 2 Drawing Sheets

RING LASER GYROSCOPE READOUT

The invention relates to a ring laser gyroscope readout, and in particular the invention relates to a ring laser gyroscope readout having three readout subassemblies with a circuit for averaging the best two out of three readings.

BACKGROUND OF THE INVENTION

The prior art ring laser gyroscope readout is described in U.S. Pat. No. 4,473,297, issued Sept. 25, 1984. Related patents include U.S. Pat. Nos. 4,257,015, issued Mar. 17, 1981, and 4,344,706, issued Aug. 17, 1982. The prior art ring laser gyroscope includes a triangular block having a triangular cavity, three mirrors disposed at respective corners of the cavity for reflecting a clockwise beam and a counterclockwise beam, one of said mirrors being a partly reflective type of mirror, and a readout assembly disposed at said partly reflective mirror, for measuring the gyroscope output.

One problem with the prior art ring laser gyroscope is that a defect in the readout subassembly causes an error in the readout reading and in the gyroscope output.

SUMMARY OF THE INVENTION

According to the present invention, a ring laser gyroscope is provided. This gyroscope comprises a triangular block having a triangular cavity, three mirrors disposed at respective corners of the cavity, each mirror being a partly reflective type of mirror for reflecting a clockwise beam and a counterclockwise beam and for passing through a part of the beams, and three readout subassemblies disposed next to the respective mirrors for obtaining three readout readings.

By using three readout subassemblies, the average of the two best readings can be obtained, and the problem of having an error in the readout reading and in the gyroscope output can be avoided.

The foregoing and other objects, features and advantages will be apparent from the following description of the preferred embodiment of the invention as illustrated in the accompanying drawings.

DESCRIPTION OF THE PREFERRED EMBODIMENT

Figure 1:
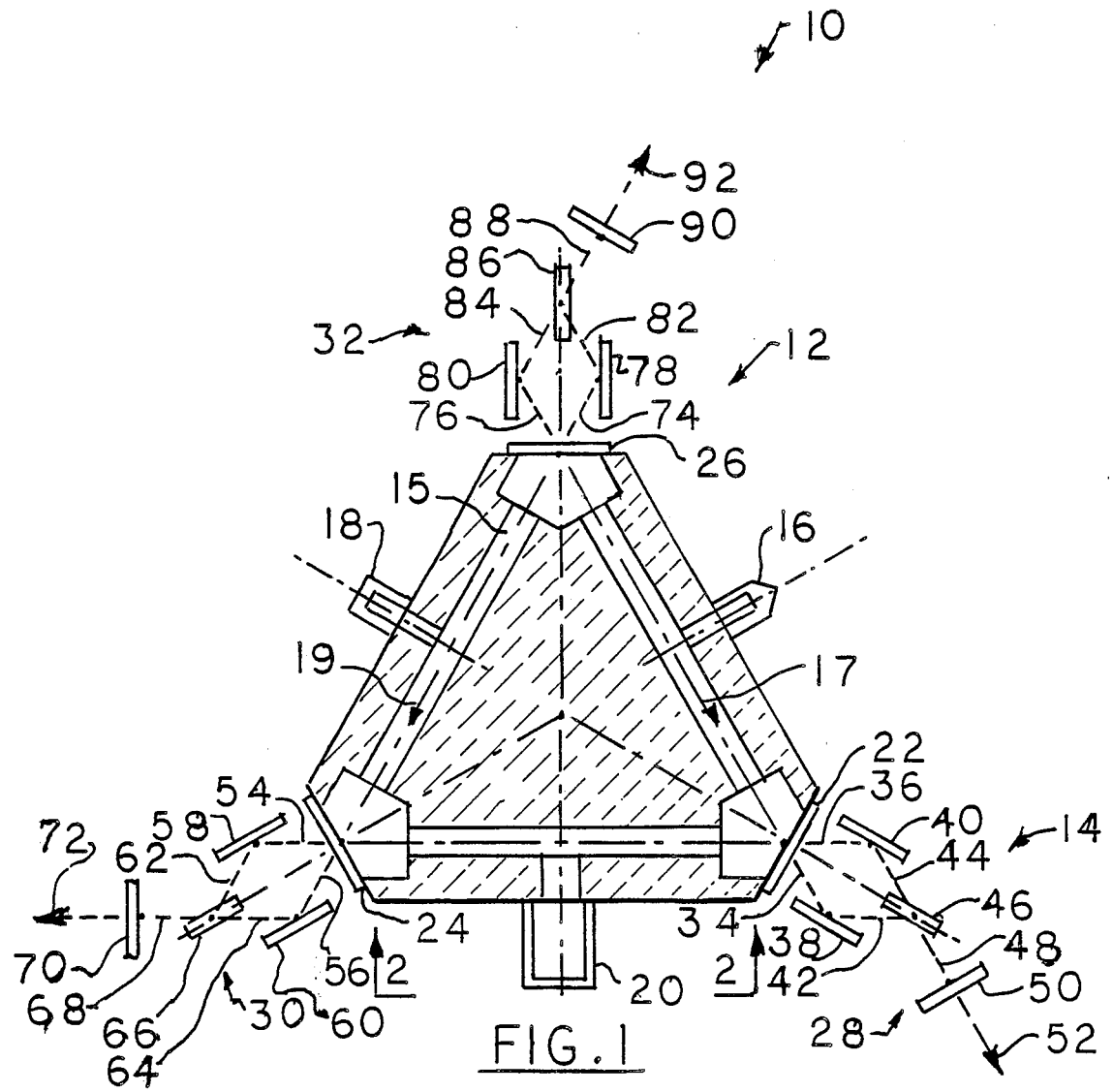
FIG. 1 is a plan section view of a ring laser gyroscope according to the invention.
Figure 2:
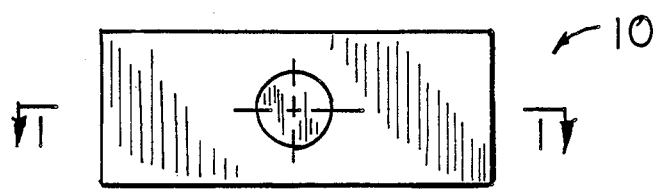
FIG. 2 is an elevation view as taken along line 2—2 of FIG. 1.

As shown in FIG. 1, a ring laser gyrsocope 10 according to the invention is provided. Gyroscope 10 includes a block assembly 12 and a readout assembly 14. Block 12 has a cavity 15. Block 12 has a first anode 16, a second anode 18, and a cathode 20. First anode 16 and cathode 20 generate a clockwise beam 17. Second anode 18 and cathode 20 generate a counterclockwise beam 19. Block 12 has a first mirror 22, a second mirror 24, and a third mirror 26. Each of the mirrors 22, 24, 26, is a partly reflective mirror, and is disposed at a respective corner of block 12.

Readout or sensor assembly 14 has a first readout subassembly 28, which is disposed adjacent to first mirror 22, and has a second readout subassembly 30, which is disposed adjacent to second mirror 30. Readout assembly 14 also has a third readout subassembly 32, which is disposed adjacent to third mirror 26, and has a signal processing subassembly 33. Readout subassemblies 28, 30, 32 are substantially identical in construction.

First readout 28 has a clockwise beam portion 34, a counterclockwise beam portion 36, a mirror 38, and a mirror 40. First readout 28 also has a reflected clockwise beam 42, a reflected counterclockwise beam 44, a beam combiner 46 with combined beams 48, a fringe detector 50, and a first output 52.

Second readout 30 has a clockwise beam portion 54, a counterclockwise beam portion 56, a mirror 58, and a mirror 60. Second readout 30 also has a reflected clockwise beam 62, a reflected counterclockwise beam 64, a beam combiner 66 with combined beams 68, a fringe detector 70, and a second output 72.

Third readout 32 has a clockwise beam portion 74, a counterclockwise beam portion 76, a mirror 78, and a mirror 80. Third readout 32 also has a reflected clockwise beam 82, a reflected counterclockwise beam 84, a beam combiner 86 with combined beams 88, a fringe detector 90, and a third output 92.

Figure 3:
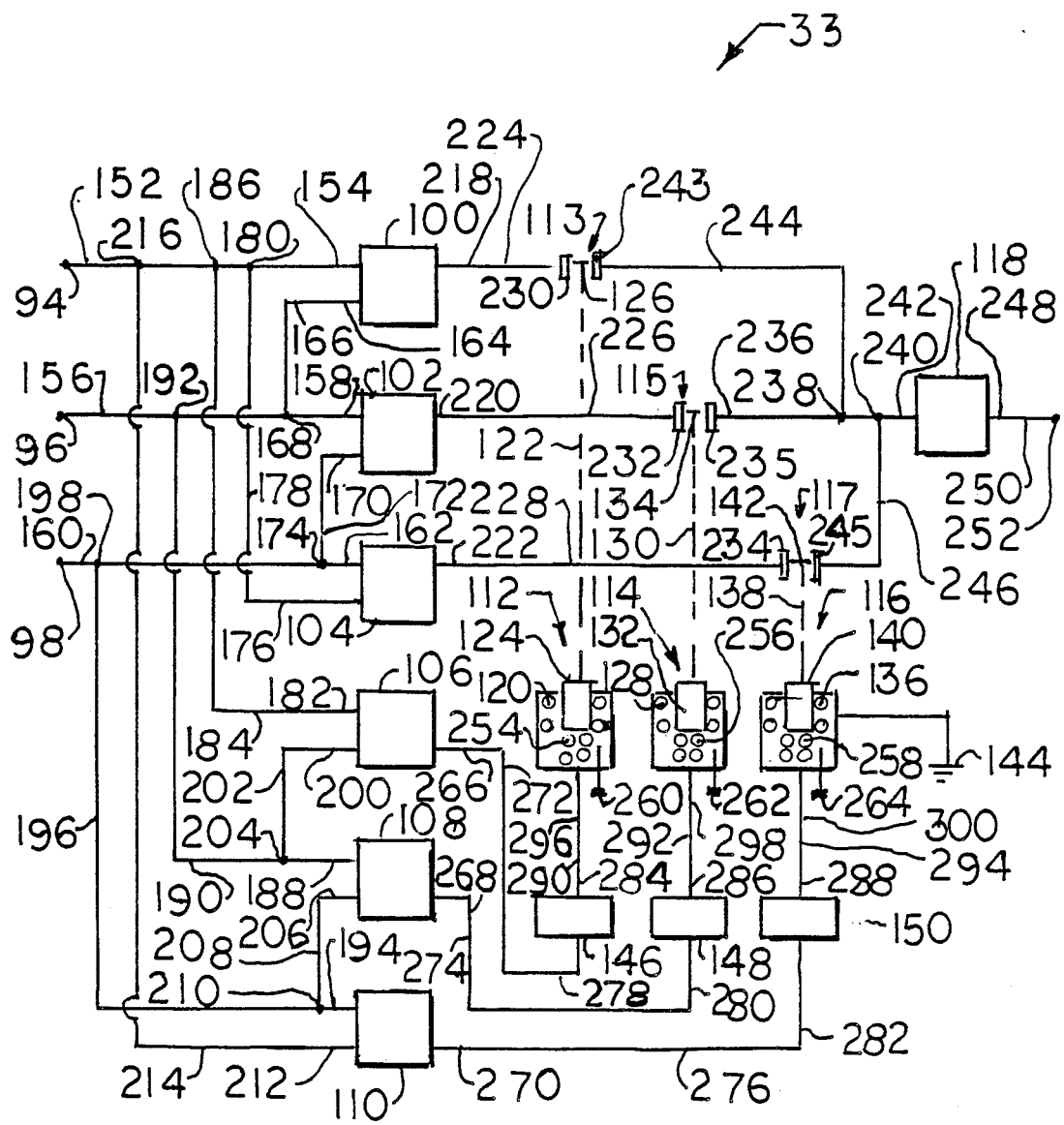
FIG. 3 is a circuit drawing of a portion of FIG. 1.

As shown in FIG. 3, the signal processing subassembly 33 has input terminals 94, 96, 98, which are respective portions of fringe detectors 50, 70, 90.

Subassembly 33 includes first, second and third adder units 100, 102, 104, and first, second and third subtractor units 106, 108, 110. Subassembly 33 also includes first, second and third switch actuators 112, 114, 116, which operate switch units 113, 115, 117, and which respectively connect to subtractor units 106, 108, 110. Subassembly 33 also includes a multiplier unit 118, which multiplies by one-half.

First switch actuator 112 includes a coil 120, a shaft 122, a magnet 124, mounted on a bottom end of shaft 122, and a switch plate 126, mounted on a top end of shaft 122. Second switch actuator 114 includes a coil 128, a shaft 130, a magnet 132, mounted on a bottom end of shaft 130, and a switch plate 134, mounted on a top end of shaft 130. Third switch actuator 116 includes a coil 136, a shaft 138, a magnet 140, mounted on a bottom end of shaft 138, and a switch plate 142, mounted on a top end of shaft 138.

Actuators 112, 114, 116 have a common ground 144; and have respective digital to analog (D/A) converters 146, 148, 150. First terminal 94 has a connector 152, which connects to a first input terminal 154 of first adder 100. Second terminal 96 has a connector 156, which connects to a first input terminal 158 of second adder 102. Third terminal 98 has a connector 160, which connects to a first input terminal 162 of third adder 104. First adder 100 has a second input terminal 164, which has a connector 166 that connects to a junction 168 on connector 156. Second adder 102 has a second input terminal 170, which has a connector 172 that connects to a junction 174 on connector 160. Third adder 104 has a second input terminal 176, which has a connector 178 that connects to a junction 180 on connector 152. First subtractor 106 has a first input terminal 182, which has a connector 184 that connects to a junction 186 on connector 152. Second subtractor 108 has a first input terminal 188, which has a connector 190 that connects to a junction 192 on connector 156. Third subtractor 110 has a first input terminal 194, which has a connector 196 that connects to a junction 198 on connector 160. First subtractor 106 has a second input terminal 200, which has a connector 202 that connects to a junction 204 on connector 190. Second subtractor 108 has a second input terminal 206, which has a connector 208 that connects to a junction 210 on connector 196. Third subtractor 110 has a second input terminal 212, which has a connector 214 that connectos to a junction 216 on connector 152. First, second and third adders 100, 102, 104 have respective output terminals 218, 220, 222, which have respective connectors 224, 226, 228 that connect to switch input terminals 230, 232, 234 of switches 113, 115, 117. Switch 115 has an output terminal 235, which has a connector 236 that extends through junction 238 and through another junction 240 to an input terminal 242 of multiplier 118. Switch 113 has an output terminal 243, which has a connector 244 that connects to junction 238. Switch 117 has an output terminal 245, which has a connector 246 that connects to junction 240. Multiplier 118 has an output terminal 248, which has a connector 250 that connects to a readout output terminal 252. Magnets 124, 132, 140 have respective tension springs 254, 256, 258, which have respective tension force adjusting screws 260, 262, 264. Springs 254, 256, 258 each has its upper coil turn fixedly attached to its respective magnet 124, 132, 140, and its lower coil turn fixedly attached to its casing for applying respective tension forces. A least difference in readout value is insufficient to lift the respective switch plate. The larger differences in readout values are sufficient to lift their switch plates. Screws are used to set a selective tension force in each of the springs 254, 256, 258. Subtractors 106, 108, 110 have respective output terminals 266, 268, 270, which have respective connectors 272, 274, 276 that connect to respective input terminals 278, 280, 282 of the digital to analog converters 146, 148, 150. Converters 146, 148, 150 have respective output terminals 284, 286, 288, which have respective connectors 290, 292, 294 that connect to respective input terminals 296, 298, 300 of the actuators 112, 114, 116.

In operation, adders 100, 102, 104 add together the digital signals of their respective two input terminals 154, 164 and 158, 170 and 162, 176. Subtractors 106, 108, 110 subtract, or find the difference, of the digital signals of their respective two input terminals 182, 200 and 188, 206 and 194, 212. Digital to analog converters 146, 148, 150 change their digital differences to analog differences, which are fed to respective coils 120, 128, 136. Springs 254, 256, 258 apply respective equal tension forces to their respective magnets 124, 132, 140. Such equal tension forces are adjustable to a different level using respective adjusting screws 260, 262, 264 for setting a tension force threshold level. In FIG. 3, the spring tension forces act downwardly. Coils 120, 128, 136 apply respective forces on magnets 124, 132, 140, which act upwardly. The actuator 112 or 114 or 116 with the smallest analog difference, or difference in readout value, will not open its switch plate; but the other two actuators with the larger analog differences, or differences in readout values, will open their switch plates. For example, if readout values at terminals 94, 96, and at subtractor 106, have the smallest difference, its switch plate 126 will not open. The digital sum of signals from terminals 94, 96 on conductor 244 is halved by multiplier 118. Thus, the average value of the signals entering terminals 94, 96 leaves at output terminal 252.

The advantages of gyroscope 10 are indicated hereafter. First, gyroscope 10 remains operational if one readout subassembly 28 or 30 or 32 fails or is defective. Second, gyroscope 10 automatically cancels out the reading from a defective readout subassembly, and uses the average of the two good subassemblies. Third, testing of the gyroscope 10 is faciliated. Fourth, reliability of gyroscope 10 is improved at a relatively small manufacturing cost. While the invention has been described in its preferred embodiment, it is to be understood that the words which have been used are words of description rather than limitation and that changes may be made within the purview of the appended claims without departing from the true scope and spirit of the invention in its broader aspects. For example, a four-sided gyroscope, instead of a three-sided gyroscope, can have the readout assembly 14.

The embodiments of an invention in which an exclusive property or right is claimed are defined as follows:

1. A ring laser gyroscope comprising:
   a block having a cavity with a plurality of corners;
   three partly reflective mirrors respectively disposed at three of the corners for reflecting a clockwise beam and a counterclockwise beam and for passing through a part of each beam at each of the three corners;
   anode means and cathode means for generating the beams;
   a readout assembly having three readout subassemblies respectively disposed adjacent to the three mirrors for receiving three respective readings; and
   selecting means for selecting the best two of the three readings.

2. The gyroscope of claim 1, including
   averaging means for finding the average value of the best two readings.

3. The gyroscope of claim 1, wherein each of the three readout subassemblies includes:
   a first mirror for reflecting the clockwise beam part;
   a second mirror for reflecting the counterwise beam part;
   a beam combiner for combining the reflected beam parts; and
   a fringe detector for providing an output reading.

4. The gyroscope of claim 3, wherein the selecting means comprises:
   first and second and third fringe detector terminals having respective first and second and third output connectors;
   first and second and third adder means having respective first and second and third input terminals connected respectively to the first and second and third detector output connectors and having respective fourth and fifth and sixth input terminals connected respectively to the second and third and first detector output connectors and having respective first and second and third output terminals having respective first and second and third output connectors;
   first and second and third subtractor means having respective first and second and third input terminals connected respectively to the first and second and third detector output connectors and having respective fourth and fifth and sixth input terminals connected respectively to the second and third and first detector output connectors and having respective first and second and third output terminals having respective first and second and third output connectors; and
   switch means having first and second and third input terminals respectively connected to the first and second and third subtractor output connectors and having respective first and second and third switch units respectively connected to the first and second and third adder output connectors.

5. The gyroscope of claim 4, wherein the first and second and third switch units respectively have first and second and third input terminals and respectively have first and second and third output terminals with respective first and second and third output connectors and respectively have first and second and third switch plates, said first and second and third switch input terminals being respectively connected to the first and second and third adder output connectors.

6. The gyroscope of claim 5, wherein the first and second and third switch plates respectively have first and second and third shafts respectively having first and second and third magnets respectively coacting with first and second and third coils respectively connected to first and second and third actuator input terminals respectively having first and second and third actuator input connectors, and wherein the first and second and third switch units respectively have first and second and third digital to analog converters having the respective first and second and third switch input terminals and having respective first and second and third output terminals respectively connected to the first and second and third actuator input connectors.

7. The gyroscope of claim 6, including a multiplier means having an input terminal connected to the first and second and third switch output connectors and having an output terminal for providing a gyroscope output reading.

8. The gyroscope of claim 1, wherein the block has three sides and has three corners.

9. A ring laser gyroscope comprising:
a multisided block having a multisided cavity with a plurality of corners;
three partly reflective mirrors respectively disposed at three of the corners for reflecting a clockwise beam and a counterclockwise beam and for passing through a portion of each beam at each of the three corners;
anode means and cathode means for generating the beams;
readout means for providing three readings respectively from the three mirrors; and
selecting means for cancelling one reading which is the least accurate of the three readings and for using the two remaining of the three readings for providing a gyroscope output reading.

10. A readout assembly for a ring laser gyroscope having a multisides block having a multisides cavity comprising:
three partly reflective mirrors respectively disposed at three corners of the cavity;
three readout subassemblies respectively disposed adjacent to the three mirrors, each subassembly having first and second reflecting mirrors and a beam combiner and a fringe detector; and
a circuit means for providing a gyroscope output having three adder means respectively connected to the fringe detectors and three subtractor means respectively connected to the three fringe detectors and switch means operated by the three subtractor means and operating the three adder means for cancelling the outputs of the two adder means which are least accurate and using the output of the remaining adder means.

11. A ring laser gyroscope comprising:
a block having a cavity with a plurality of corners;
three partly reflective mirrors respectively disposed at three of the corners for reflecting a clockwise beam and a counterclockwise beam and for passing through a part of each beam at each of the three corners;
anode means and cathode means for generating the beams;
a readout assembly having three readout subassemblies respectively disposed adjacent to the three mirrors for receiving three respective readings;
selecting means for selecting the best two of the three readings; and
averaging means for finding the average value of the two readings; wherein
each readout subassembly includes:
a first mirror for reflecting the clockwise beam part;
a second mirror for reflecting the counterclockwise beam part;
a beam combiner for combining the reflected beam parts; and
a fringe detector for providing an output reading; and wherein
the selecting means comprises:
first and second third fringe detector terminals having respective first and second and third output connectors;
first and second and third adder means having respective first and second and third input terminals connected respectively to the first and second and third detector output connectors and having respective fourth and fifth and sixth input terminals connected respectively to the second and third and first detector output connectors and having respective first and second and third output terminals having respective first and second and third output connectors;
first and second and third subtractor means having respective first and second and third input terminals connected respectively to the first and second and third detector output connectors and having respective fourth and fifth and sixth input terminals connected respectively to the second and third and first detector output connectors and having respective first and second and third output terminals having respective first and second and third output connectors; and
switch means having first and second and third input terminals respectively connected to the first and second and third subtractor output connectors and having respective first and second and third switch units respectively connected to the first and second and third adder output connectors; wherein
the first and second and third switch units respectively have first and second and third input terminals and respectively have first and second and third output terminals with respective first and second and third output connectors and respectively have first and second and third switch plates, said first and second and third switch input terminals being respectively connected to the first and second and third adder output connectors.

12. A method of measuring an angular rate, including:
spinning about a rotation axis a clockwise laser beam and a counterclockwise laser beam which are disposed within a multisided cavity of a ring laser gyroscope having corners with three partly reflective mirrors;

extracting portions of the beams at each partly reflective mirror;
measuring the difference of the lengths of the beam portions at each partly reflective mirror for reading the angular rate of the gyroscope about the rotation axis at each mirror to provide first and second and third readings;
determining the two of the readings which are closest together; and
finding the average of the two readings for use as the gyroscope output reading of angular rate.

* * * * *